United States Patent
Beesley et al.

(10) Patent No.: US 11,110,471 B2
(45) Date of Patent: Sep. 7, 2021

(54) PLUG-IN OIL DIFFUSER WITH NON-PLASTIC COVER

(71) Applicant: Candle Warmers Etc., Draper, UT (US)

(72) Inventors: Brian K. Beesley, Draper, UT (US); Meghan Saunders, Draper, UT (US)

(73) Assignee: Candle Warmers Etc., Draper, UT (US)

( * ) Notice: Subject to any disclaimer, the term of this patent is extended or adjusted under 35 U.S.C. 154(b) by 455 days.

(21) Appl. No.: 16/190,880

(22) Filed: Nov. 14, 2018

(65) Prior Publication Data

US 2019/0168240 A1    Jun. 6, 2019

Related U.S. Application Data

(60) Provisional application No. 62/593,710, filed on Dec. 1, 2017.

(51) Int. Cl.
| | | |
|---|---|---|
| *A61L 9/03* | (2006.01) | |
| *A61L 9/12* | (2006.01) | |
| *B05B 1/24* | (2006.01) | |
| *F21V 33/00* | (2006.01) | |
| *F21V 23/06* | (2006.01) | |
| *F21Y 115/10* | (2016.01) | |

(52) U.S. Cl.
CPC ............... *B05B 1/24* (2013.01); *A61L 9/03* (2013.01); *F21V 23/06* (2013.01); *F21V 33/0004* (2013.01); *A61L 9/12* (2013.01); *A61L 2209/12* (2013.01); *A61L 2209/133* (2013.01); *F21Y 2115/10* (2016.08)

(58) Field of Classification Search
None
See application file for complete search history.

(56) References Cited

U.S. PATENT DOCUMENTS

| | | | | | |
|---|---|---|---|---|---|
| 2,714,649 | A | * | 8/1955 | Critzer ................. | A01M 1/2083 |
| | | | | | 392/392 |
| 2,733,333 | A | * | 1/1956 | Peters ................. | A01M 1/2083 |
| | | | | | 392/393 |
| 3,780,260 | A | * | 12/1973 | Elsner .................. | H05B 3/0033 |
| | | | | | 392/392 |
| 3,948,445 | A | * | 4/1976 | Andeweg ............ | A01M 1/2066 |
| | | | | | 239/53 |
| 5,136,684 | A | * | 8/1992 | Lonker ..................... | A61L 9/03 |
| | | | | | 261/DIG. 89 |
| 5,220,636 | A | * | 6/1993 | Chang ....................... | A61L 9/03 |
| | | | | | 261/DIG. 88 |
| 5,373,581 | A | * | 12/1994 | Smith ................. | A01M 1/2077 |
| | | | | | 219/202 |
| 5,647,052 | A | * | 7/1997 | Patel ......................... | A61L 9/03 |
| | | | | | 392/390 |

(Continued)

*Primary Examiner* — Thor S Campbell
(74) *Attorney, Agent, or Firm* — Thorpe, North & Western, LLP

(57) ABSTRACT

A plug-in oil diffuser comprises a plug extending from a housing to be plugged into a wall electrical outlet. A non-plastic faceplate is removably coupled to the housing. The non-plastic faceplate has a cavity therein with an opening to receive at least a portion of the housing. An annular insert is disposed in the opening of the non-plastic faceplate and has an exterior secured to the opening of the non-plastic faceplate and an interior removably secured to the housing.

20 Claims, 4 Drawing Sheets

(56) References Cited

U.S. PATENT DOCUMENTS

| | | | | |
|---|---|---|---|---|
| 5,796,914 | A * | 8/1998 | Gatzemeyer | A01M 1/2077 392/390 |
| 5,903,710 | A * | 5/1999 | Wefler | A01M 1/2077 392/392 |
| 5,945,094 | A * | 8/1999 | Martin | A01M 1/2077 424/76.1 |
| 6,044,202 | A * | 3/2000 | Junkel | A61L 9/03 239/135 |
| 6,085,026 | A * | 7/2000 | Hammons | A61L 9/03 392/390 |
| 6,123,935 | A * | 9/2000 | Wefler | A61L 9/037 424/76.1 |
| 6,249,645 | B1 * | 6/2001 | Smith | A61L 9/03 392/390 |
| 6,381,408 | B1 * | 4/2002 | Jaworski | A01M 1/2077 392/390 |
| 6,968,124 | B1 * | 11/2005 | Varanasi | A01M 1/2077 392/392 |
| 7,544,332 | B2 * | 6/2009 | De Silva | A61L 9/035 422/125 |
| 7,670,566 | B2 * | 3/2010 | Adair | A01M 1/2077 422/125 |
| 8,983,279 | B2 * | 3/2015 | Adair | A61L 9/037 392/395 |
| 10,064,969 | B2 * | 9/2018 | Hsiao | F21V 17/104 |
| 2003/0156830 | A1 * | 8/2003 | Cox | A01M 1/2077 392/390 |
| 2004/0005146 | A1 * | 1/2004 | Wefler | A61L 9/03 392/392 |
| 2004/0190883 | A1 * | 9/2004 | Kompara | A61L 9/035 392/390 |
| 2007/0237498 | A1 * | 10/2007 | Helf | A01M 1/2077 392/386 |
| 2008/0056691 | A1 * | 3/2008 | Wingo | A61L 9/127 392/395 |
| 2014/0037273 | A1 * | 2/2014 | Jaworski | A61L 9/037 392/390 |
| 2014/0205272 | A1 * | 7/2014 | Midgette | A01M 1/2077 392/395 |

* cited by examiner

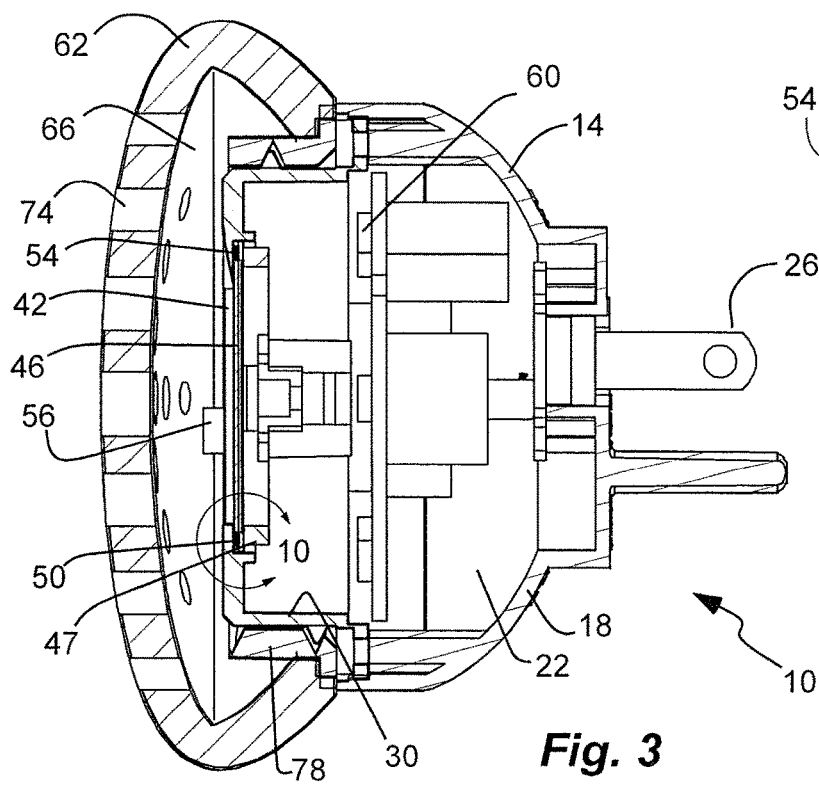
Fig. 3
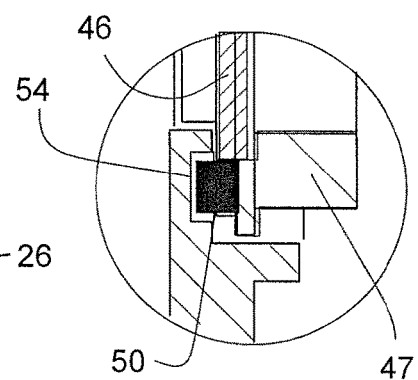
Fig. 10
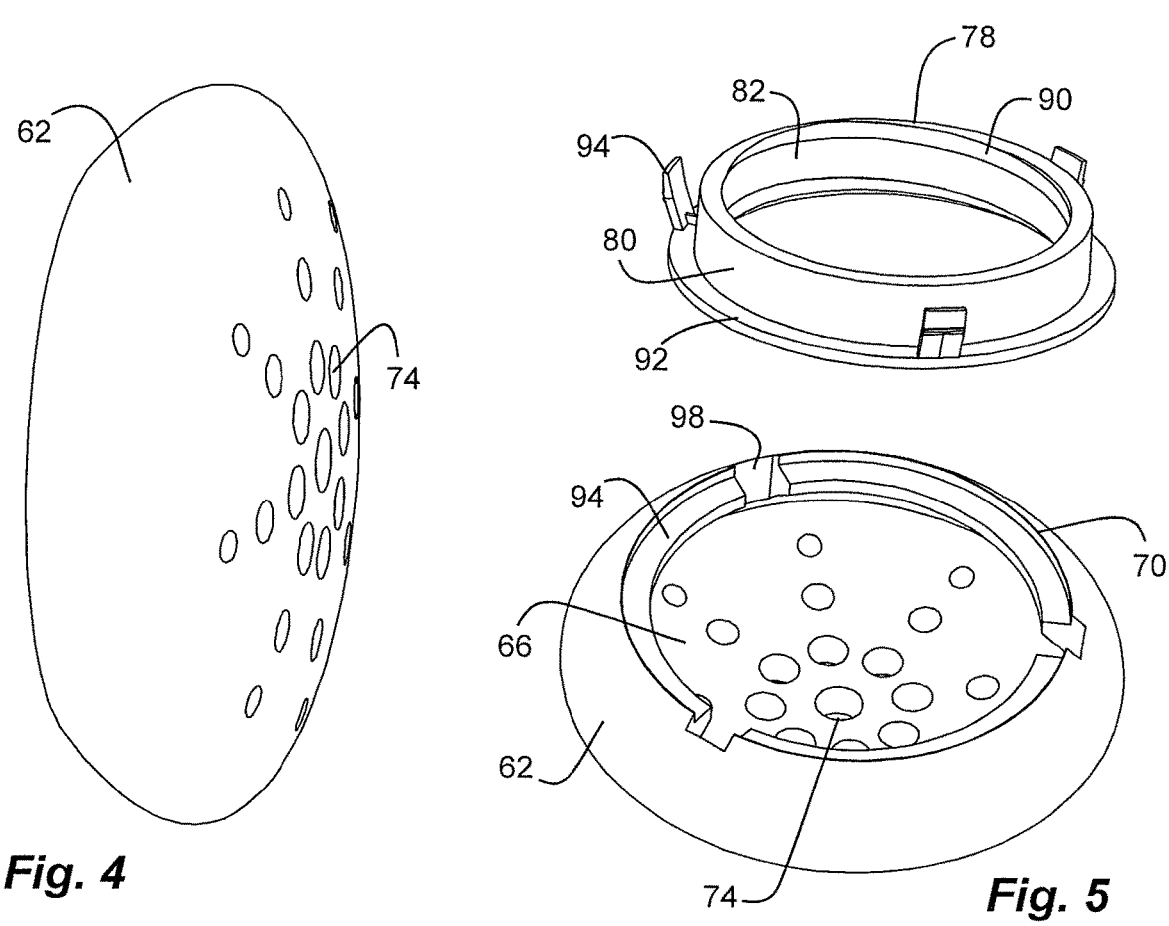
Fig. 4
Fig. 5

PLUG-IN OIL DIFFUSER WITH NON-PLASTIC COVER

PRIORITY CLAIM

Priority is claimed to U.S. Provisional Patent Application Ser. No. 62/593,710, filed Dec. 1, 2017, which is hereby incorporated herein by reference.

BACKGROUND

Oil diffusers diffuse oil into the ambient air for providing scent, fragrance or aroma to the air. Such oil diffusers can be used with aromatherapy or essential oils. The oil can be diffused by various means, including evaporation; heat assisted evaporation through a heat source, candle, or boiling; ultrasonic diffusion with water and ultrasonic waves; and a nebulizer that breaks the oil into molecules for dispersion. Many diffusers have a plastic housing that is aesthetically unappealing.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein:

FIG. 3 is a cross-sectional side view of the oil diffuser of FIG. 1.

FIG. 4 is a perspective side view of the faceplate of the oil diffuser of FIG. 1.

FIG. 5 is a perspective exploded view of the faceplate of the oil diffuser of FIG. 1, shown with an annular insert removed from the faceplate.

FIG. 10 is a detailed cross-sectional side view of the oil diffuser of FIG. 1, taken along line 10 of FIG. 3.

Figure 1:
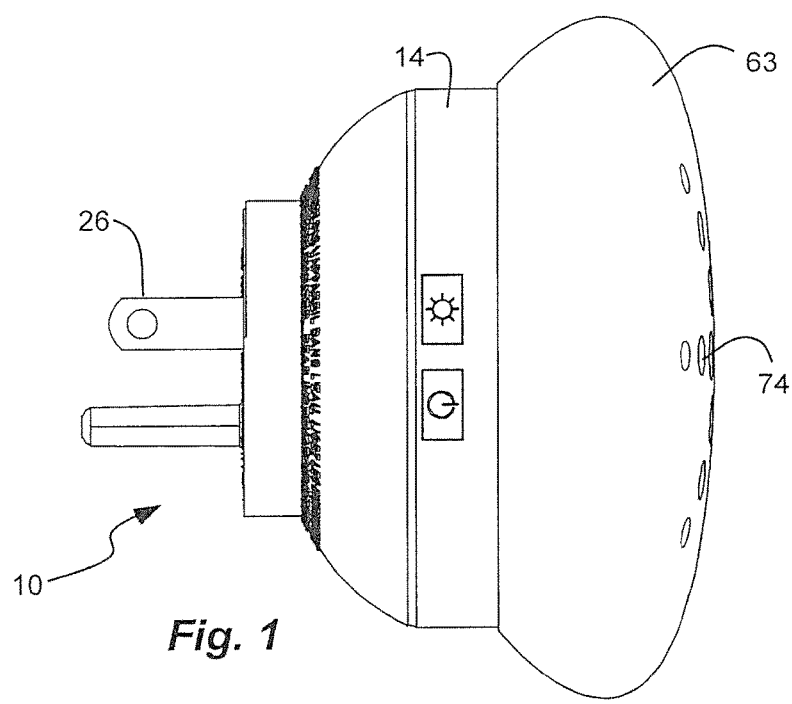
FIG. 1 is a side view of plug-in oil diffuser in accordance with an embodiment of the invention.
Figure 2:
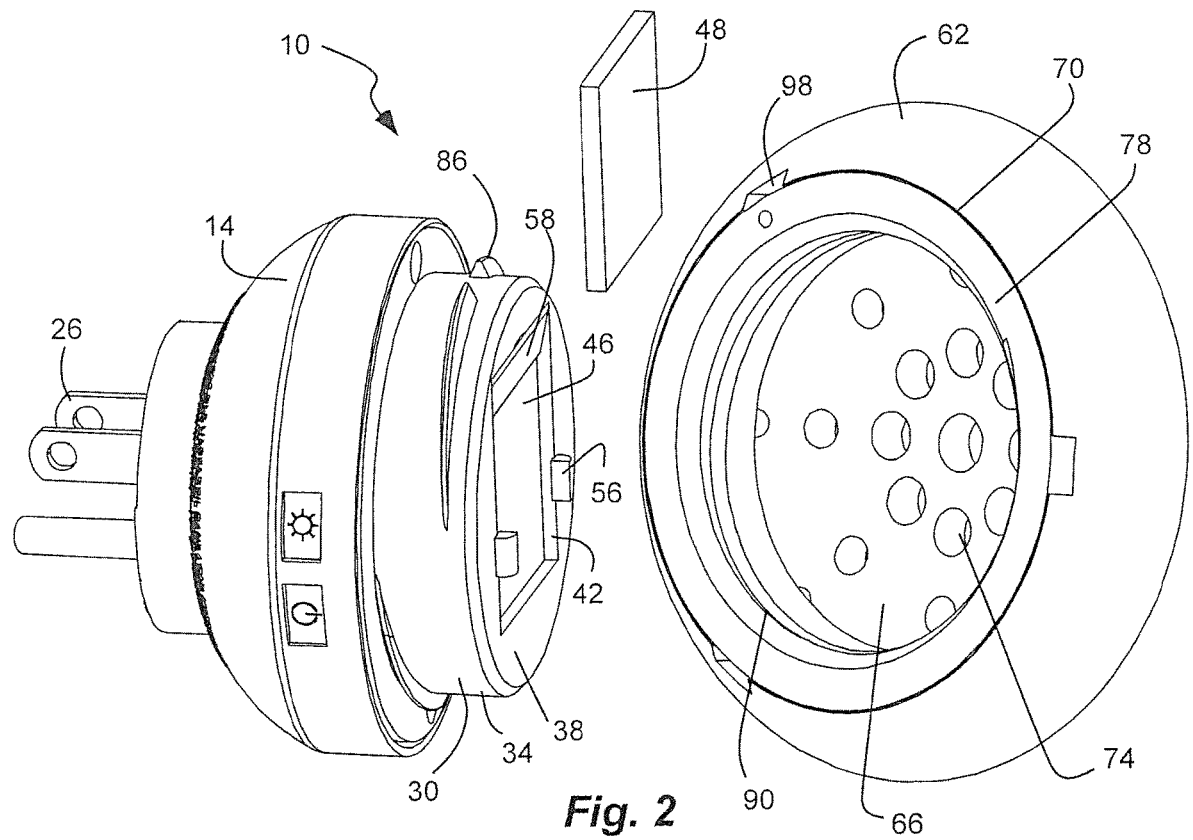
FIG. 2 is a schematic exploded view of the oil diffuser of FIG. 1, shown with a faceplate and a pad removed from a housing.
Figure 6:
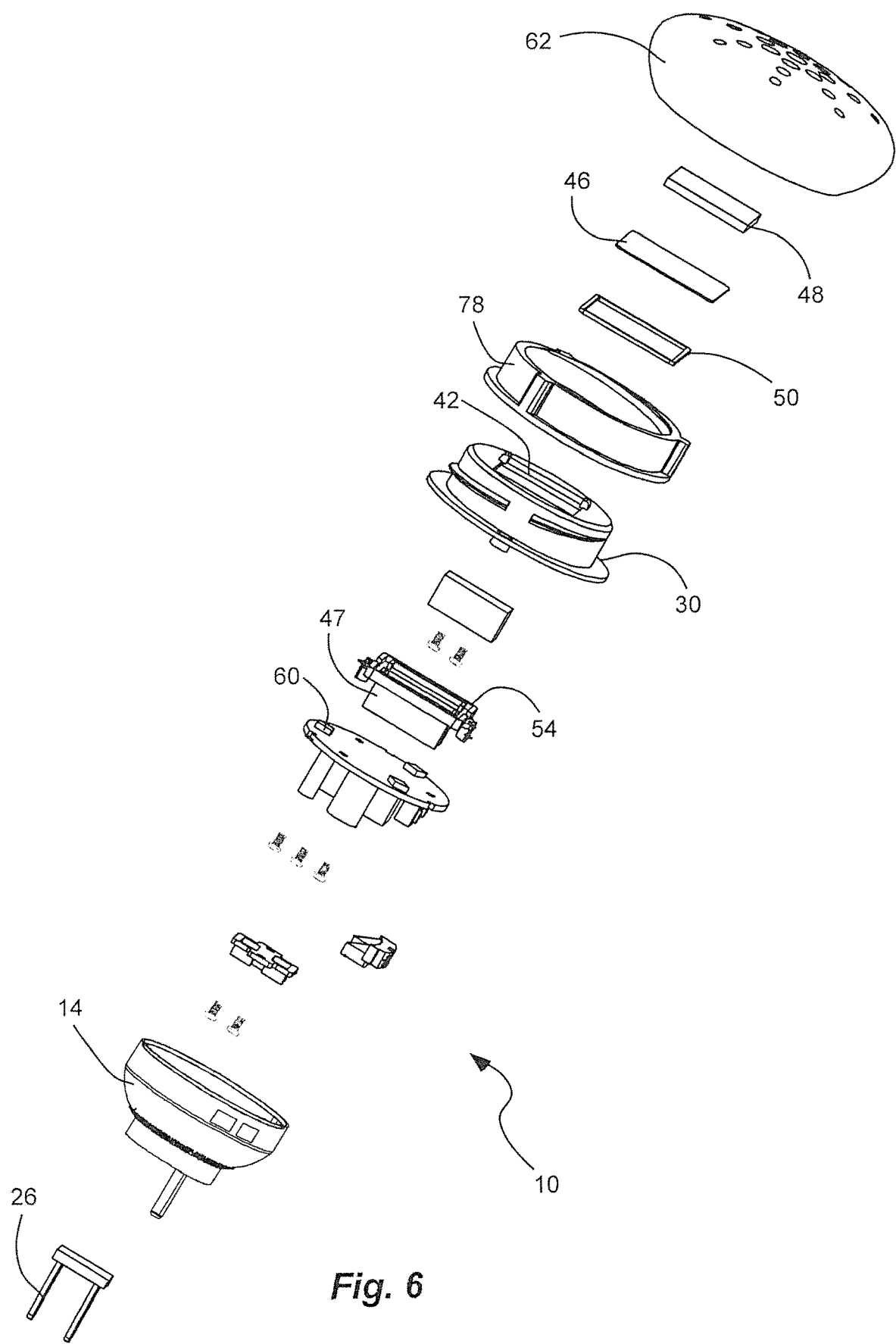
FIG. 6 is an exploded view of the oil diffuser of FIG. 1.

Reference will now be made to the exemplary embodiments illustrated, and specific language will be used herein to describe the same. It will nevertheless be understood that no limitation of the scope of the invention is thereby intended.

DETAILED DESCRIPTION

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

The term "diffuser" is used broadly herein to refer to any type of oil dispersion means, including diffusers and nebulizers. The term "oil" is used broadly herein to refer to any type of oil, including scented or fragrant oil, and so called "essential" oils.

An initial overview of the inventive concepts are provided below and then specific examples are described in further detail later. This initial summary is intended to aid readers in understanding the examples more quickly, but is not intended to identify key features or essential features of the examples, nor is it intended to limit the scope of the claimed subject matter.

The invention presents an oil diffuser type air freshener for providing a desired fragrance or scent to the surrounding environment. In addition, the air freshener or the oil diffuser is a plug-in type that is plugged into a standard, residential electrical outlet that provides both electrical power and physical support for the diffuser. The oil diffuser diffuses oil. The oil can be absorbed or impregnated into an absorbent pad, which can be removably and replacably carried by the diffuser. The diffuser can heat the pad to assist in evaporating the oil. In addition, the diffuser can heat the pad with a heat plate. A seal can be located between the heat plate and the housing to resist oil seepage from the pad in to the housing. In addition, the diffuser can have a housing and a faceplate carried by the housing, and sized and shaped to substantially cover or shield the housing when viewed straight on. The faceplate can present an aesthetically pleasing appearance. The faceplate can be non-plastic, such as ceramic. The faceplate can comprise a cavity or hollow with an opening thereto. An insert can be located in the opening of the faceplate and carried by the faceplate to secure the faceplate to the housing.

Referring to FIGS. 1-6, a plug-in oil diffuser device, indicated generally at 10, in an example implementation in accordance with an embodiment of the invention is shown for diffusing fragrant oil. The diffuser 10 comprises a housing 14 that can contain or carry all or substantially all of the components of the diffuser. In one aspect, the housing 14 can be formed of plastic, and can be formed by injection molding. In another aspect, the housing 14 can be formed by a pair of housing halves joined together. The housing 14 can have walls 18 defining a hollow 22 therein. A plug 26 can extend from the housing 14. The plug 26 can be a standard, residential electrical plug with prongs that can be plugged into a standard, residential, wall electrical outlet. Thus, the housing 14 and the diffuser 10 can be carrier by the wall electrical outlet and suspended on the wall. The plug 26 can comprise a pair of electrical leads, positive and negative, and a prong that can be received in the ground of the outlet. In addition, the housing 14 can have a projection 30 extending from the housing opposite the plug 26. The projection 30 can have an exterior 34. In one aspect, the projection 30 can be cylindrical, and can have a diameter narrower than a width or diameter of the housing 14 from which it extends. In one aspect, the projection 30 can be plastic and can define one half or portion that can be coupled to the other half or portion of the housing to form the housing 14. A circuit board, or other control electronics, can be disposed in the hollow 22 of the housing 14 for controlling operation of the diffuser 10. One or more buttons can be carried by the housing 14 and electrically coupled to the circuit board or other control electronics.

The housing 14 and the projection 30 can have a face 38 facing outwardly opposite the plug 26. The face 38 can be vertically oriented when the housing 14 and the diffuser 10 are plugged into the wall electrical outlet. An aperture 42 can be formed in the face 38 of the housing 14. A heat plate 46 is carried by and disposed in the housing 14, and is electrically coupled to the plug 26, and the circuit board or control electronics in the housing. In addition, the heat plate 46 is positioned at the aperture 42 of the housing 14 so that the heat plate 46 is exposed with respect to the housing 14. Unless otherwise indicated, the term "heat plate" is used herein to refer both to the metal heat plate itself, and any mount structure or support plate 47 that carries the metal heat plate. The heat plate 46, and any mount structure or support plate 47, can span and close the aperture 42 in the housing 14. The aperture 42 can expose the heat plate 46. The heat plate 46 receives the absorbent pad 48 with oil therein. The heat plate 46 can comprise an electrically resistive heater that generates heat from electricity provided by the plug 26 and the circuit board or control electronics, thus selectively heating the heat plate 46 to a predetermined temperature. The selective application of heat can promote controlled evaporation of the oil in the pad 48. The projection 30 and the face 38 can surround the heat plate 46. The heat plate 46, and any mount structure or support plate 47, can abut an interior of the face 38 around a perimeter of the aperture 42. In one aspect, the heat plate 46 can be recessed with respect to the face 38 to form a pocket to receive the pad 48. A seal 50 or gasket can be disposed between the heat plate 46, and any mount structure or support plate 47, and the face 38 or wall 18 to resist oil seepage from the pad 48 into the housing 14, and thus electronics disposed in the housing 14. In one aspect, a groove 54 can be formed in the interior of the face 38, and can circumscribe the aperture 42, to receive the seal 50 or gasket. In one aspect, the pad 48 abuts the heat plate 46. The heat plate 46 can be vertically oriented along with the face 38. A chamfer 58 can be formed in the face 38 at the perimeter of the aperture 42 to assist with insertion and remove of the pad 48 to and from the pocket. In addition, tabs 56 can be disposed around a perimeter of the aperture 42 and extending over the aperture to hold the pad 48 against the heat plate 46.

As described above, the diffuser 10 or the housing 14 can have control electronics, such as a PCB, disposed in the housing 14. In one aspect, a light source 60 can be disposed in the housing 14 and electrically coupled to the plug 26 via the control electronics. The light source 60 can include one or more LEDs. In one aspect, at least a portion of the housing 14, including at least a portion of the face 38 or the projection 30, is at least translucent to pass light from the light source 60 therethrough. The light from the light source 60 can provide an aesthetically pleasing appearance, and can enhance the therapeutic operation of the diffuser 10 along with the aroma.

The diffuser 10 can also have a faceplate 62 coupled to the housing 14, or the projection 30 thereof. The faceplate 62 can have a width or diameter greater than a width or diameter of the housing 14 in order to cover and hide the housing 14 when viewed straight on. In addition, the faceplate 62 can be non-plastic. In one aspect, the faceplate 62 can be or can comprise ceramic that is fire hardened and glazed. Forming just the faceplate 62 of ceramic can reduce the weight of the diffuser so that the plug 26 can maintain the weight of the diffuser 10 in the wall electrical socket. In one aspect, the faceplate 62 can have a weight greater than a remaining weight of the diffuser 10 without the faceplate. In addition, the faceplate 62 can have a wall thickness greater than a wall thickness of the housing 14. Thus, the faceplate 62 can provide an appearance of a more substantial structure, such as a pottery or ceramic. The faceplate 62 can also cover the face 38, the heat plate 46 and the pad 48 for a more aesthetically pleasing appearance. The faceplate 62 can be removably coupled to the projection 30 of the housing 14 to allow access to and replacement of the pad 48.

The faceplate 62 can have a cavity or hollow 66 therein to receive the projection 30, the heat plate 46, and the pad 48. An opening 70 can be formed in the faceplate 62 and into the cavity 66 to receive the projection 30 of the housing 14 therethrough. One or more holes 74 can be formed in the faceplate 62, opposite the opening 70, to allow release of fragrance from the pad 48, and light from the light source 60.

An annular insert 78 can be disposed in the opening 70 of the faceplate 62. The insert 78 can have an exterior 80 secured to the opening 70 of the faceplate 62. In one aspect, the insert 78 can be adhered to the faceplate 62 and in the opening 70 thereof. In addition, the insert 78 can have an interior 82 removably secured to the exterior 34 of the projection 30 of the housing 14. A releasable fastener can be formed between the interior 82 of the annular insert 78 and the exterior 34 of the projection 30 of the housing 14. In one aspect, the fastener can comprise a threaded fastener with exterior screw 86 threads formed on the projection 30 and interior screw threads 90 formed in the interior 82 of the insert 78. In another aspect, the fastener can comprise a twist-and-lock tab-and-slot, with tabs extending from the projection 34 of the housing 14 or projection 30 and received in slots in the insert 78, or vis-versa. The insert 78 can be formed of plastic, and can be formed by injection molding. The insert 78 can provide the faceplate 62 with a releasable fastener, such as screw threads, which can be easier to fabricate in the plastic insert 78 than in the ceramic faceplate 62. In addition, the insert 78 can reduce the weight of the faceplate 62, and thus the strain on the plug 26 and the connection to the wall electrical outlet. In another aspect, the insert 78 can have an annular flange 92 that can abut to an annular step 94 in the opening 70 of the faceplate 62 to control insertion depth of the insert 78 into the faceplate 62. In one aspect, the exterior of the insert 78 and the flange 92 can be flush with the exterior of the opening 70 or the faceplate 62 so that the faceplate 62 properly mates with the projection 30 or the housing 14.

In another aspect, a notch and tab can be formed between the exterior 80 of the annular insert 78 and the opening 70 of the faceplate 62 to hold the insert 78 and the faceplate 62 together, such as when screwing the faceplate 62 onto, or off of, the housing 14 or the projection 30. In one aspect, the tab 94 can be formed on the insert 78 and can extend into the notch 98 formed in the opening 70 of the faceplate 62. In another aspect, the tab can be formed in the faceplate and can extend into the notch formed in the projection of the housing. In another aspect, the notch and tab between the annular insert and the non-plastic faceplate includes multiple tabs disposed in multiple notches. The tabs and notches can be arranged non-symmetrically or asymmetrical about an axis of the faceplate 62, such as the rotational axis. Thus, the asymmetrical tabs and notches can form a keyed fit with a single orientation between the insert and the non-plastic faceplate. In combination with the releasable fastener or screw threads, the asymmetrical tabs and notches can orient the faceplate 62 with respect to the housing 14 (with the plug defining an upright orientation). Thus, indicia and/or a hole pattern of the faceplate 62 can be oriented upright. In another aspect, the tabs can extend from the faceplate and can be received in notches in the insert. In another aspect, the tabs 94 can be flexible fingers extending from the exterior 80 of the annular insert 78 and into notch 98 in an the opening 70 of the faceplate 62. The flexible fingers can be biased outwardly and abut to the opening 70 of the faceplate 62 to hold the insert 78 while an adhesive dries. The tabs 94 or the flexible fingers can have exterior teeth to engage the opening 70 of the faceplate 62.

In one aspect, the oil diffuser 10 can have separate buttons for power and control of the light source 60. A light button can control color and/or brightness of the light source.

Figure 7:
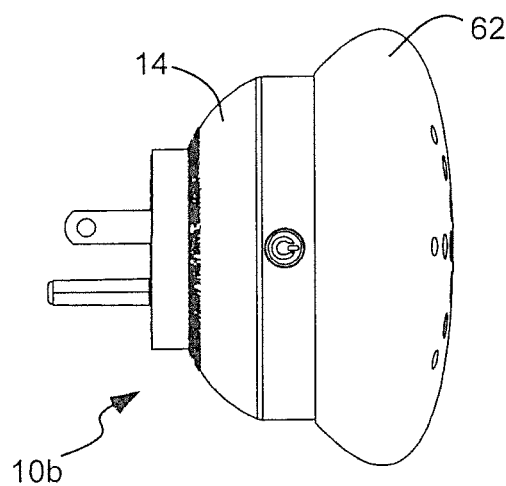
FIG. 7 is a side view of another plug-in oil diffuser in accordance with another embodiment of the invention.
Figure 8:
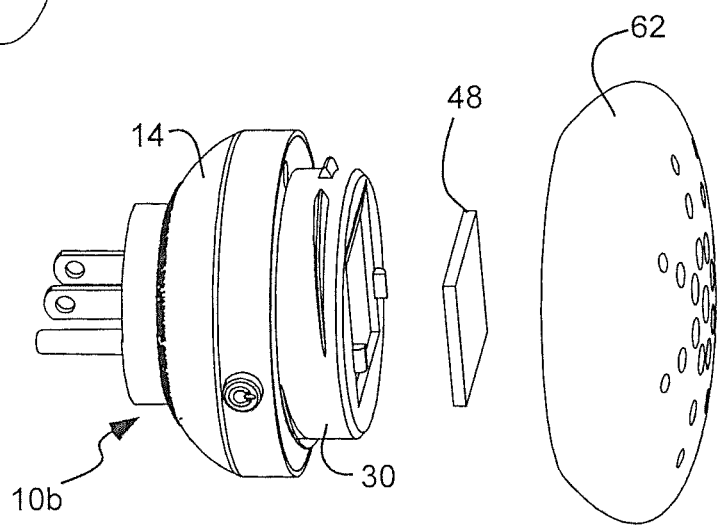
FIG. 8 is a schematic exploded view of the oil diffuser of FIG. 7.
Figure 9:
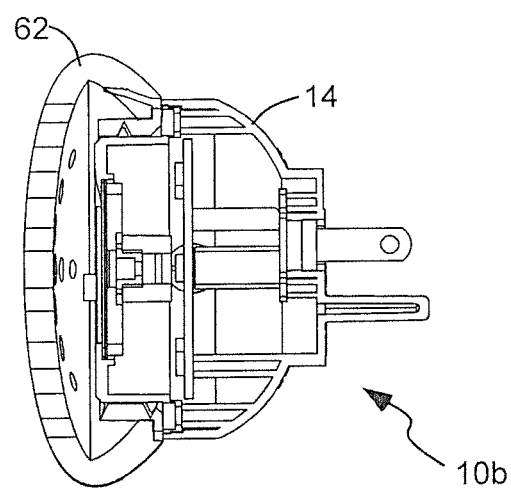
FIG. 9 is a cross-sectional side view of the oil diffuser of FIG. 7.

Referring to FIGS. 7-9, another oil diffuser 10b is shown that is similar in many respects to that described above, and which description is incorporated herein by reference. Rather than multiple control buttons, the oil diffuser 10b can have a single power button.

It is to be understood that the examples set forth herein are not limited to the particular structures, process steps, or materials disclosed, but are extended to equivalents thereof as would be recognized by those ordinarily skilled in the relevant arts. It should also be understood that terminology employed herein is used for the purpose of describing particular examples only and is not intended to be limiting.

Furthermore, the described features, structures, or characteristics may be combined in any suitable manner in one or more examples. In the description, numerous specific details are provided, such as examples of lengths, widths, shapes, etc., to provide a thorough understanding of the technology being described. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the foregoing examples are illustrative of the principles of the invention in one or more particular applications, it will be apparent to those of ordinary skill in the art that numerous modifications in form, usage and details of implementation can be made without the exercise of inventive faculty, and without departing from the principles and concepts described herein. Accordingly, it is not intended that the invention be limited, except as by the claims set forth below.

What is claimed is:

1. A plug-in oil diffuser device, comprising:
    a) a housing;
    b) a plug extending from the housing and configured to be plugged into a wall electrical outlet;
    c) a non-plastic faceplate removably coupled to the housing;
    d) the non-plastic faceplate having cavity therein with an opening to receive at least a portion of the housing;
    e) an annular insert carried by the non-plastic faceplate in the opening of the non-plastic faceplate, the annular insert securing the non-plastic faceplate to the housing, and the annular insert having an exterior secured to the non-plastic faceplate and an interior removably secured to the housing; and
    f) a notch and a tab between the annular insert and the non-plastic faceplate, with the tab extending from one of the annular insert or the non-plastic faceplate and into a notch in the other of the non-plastic faceplate or the annular insert.

2. The device in accordance with claim 1, wherein the notch and the tab between the annular insert and the non-plastic faceplate includes tabs disposed in notches; and wherein the tabs and notches are arranged non-symmetrically to form a keyed fit with a single orientation between the insert and the non-plastic faceplate, and thus orienting the non-plastic faceplate with respect to the housing and the plug defining an upright orientation.

3. The device in accordance with claim 1, further comprising:
    a flexible finger extending from the exterior of the annular insert and into a notch in an the opening of the non-plastic faceplate.

4. The device in accordance with claim 1, further comprising:
    an annular step in the opening of the faceplate;
    an annular flange on the exterior of the annular insert and abutting to the annular step.

5. The device in accordance with claim 4, wherein the insert and the faceplate are flush with one another at the opening of the faceplate.

6. The device in accordance with claim 1, further comprising:
    a releasable fastener formed between the interior of the annular insert and the housing.

7. The device in accordance with claim 6, wherein the releasable fastener formed between the interior of the annular insert and the exterior of the projection of the housing comprises a threaded fastener with exterior screw threads formed on the projection and interior screw threads formed in the insert.

8. The device in accordance with claim 1, further comprising:
    a) a projection extending from the housing opposite the plug, and having an exterior;
    b) the non-plastic faceplate removably coupled to the projection of the housing; and
    c) the opening of the non-plastic faceplate receiving the projection of the housing.

9. The device in accordance with claim 1, further comprising:
    a) a face of the housing facing outwardly opposite the plug, the face being vertically oriented;
    b) an aperture in the face of the housing;
    c) a heat plate disposed in the housing and electrically coupled to the plug, the heat plate spanning the aperture in the housing and the aperture exposing the heat plate, the heat plate configured to receive an absorbent pad with oil therein, the heat plate being vertically oriented;
    d) the heat plate abutting an interior of the face around a perimeter of the aperture; and
    e) a seal disposed between the heat plate and the face configured to resist oil seepage from the pad into the housing.

10. The device in accordance with claim 1, further comprising:
    a) a face of the housing facing outwardly opposite the plug, the face being vertically oriented;
    b) an aperture in the face of the housing;
    c) a heat plate disposed in the housing and electrically coupled to the plug, the heat plate spanning the aperture in the housing and the aperture exposing the heat plate, the heat plate configured to receive an absorbent pad with oil therein, the heat plate being vertically oriented;
    d) the heat plate being recessed with respect to the face; and
    e) a chamfer in the face at the perimeter of the aperture configured to assist insertion and remove of the pad.

11. The device in accordance with claim 1, further comprising:
   a) a light source disposed in the housing and electrically coupled to the plug; and
   b) holes in the non-plastic faceplate opposite the opening configured to allow release of light from the light source.

12. The device in accordance with claim 1, further comprising:
   a) a light source disposed in the housing and electrically coupled to the plug;
   b) at least a portion of the housing, including a portion disposed inside the non-plastic faceplate, is at least translucent and configured to pass light from the light source therethrough; and
   c holes in the non-plastic faceplate opposite the opening configured to allow release light from the light source.

13. The device in accordance with claim 1, wherein the non-plastic faceplate comprises ceramic and the annular insert comprises plastic.

14. The device in accordance with claim 1, wherein the non-plastic faceplate has a wall thickness greater than a wall thickness of the housing.

15. The device in accordance with claim 1, wherein the faceplate has a weight greater than a remaining weight of the device without the faceplate.

16. A plug-in oil diffuser device, comprising:
   a) a housing;
   b) a plug extending from the housing and configured to be plugged into a wall electrical outlet;
   c) a face of the housing facing outwardly opposite the plug, the face being vertically oriented;
   d) an aperture in the face of the housing;
   e) a heat plate disposed in the housing and electrically coupled to the plug, the heat plate spanning the aperture in the housing and the aperture exposing the heat plate, the heat plate configured to receive an absorbent pad with oil therein, the heat plate being vertically oriented;
   f) the heat plate abutting an interior of the face around a perimeter of the aperture; and
   g) a groove formed in the interior of the face an circumscribing the aperture;
   h) a seal disposed in the groove and between the heat plate and the face configured to resist oil seepage from the pad into the housing.

17. The device in accordance with claim 16, further comprising:
   a chamfer in the face at the perimeter of the aperture configured to assist insertion and remove of the pad.

18. The device in accordance with claim 16, further comprising:
   a) a non-plastic faceplate removably coupled to the housing;
   b) the non-plastic faceplate having cavity therein with an opening to receive at least a portion of the housing;
   c) an annular insert carried by the non-plastic faceplate in the opening of the non-plastic faceplate, the annular insert securing the non-plastic faceplate to the housing, and the annular insert having an exterior secured to the non-plastic faceplate and an interior removably secured to the housing; and
   d) a releasable fastener formed between the interior of the annular insert and the housing.

19. The device in accordance with claim 17, wherein the non-plastic faceplate comprises ceramic and the annular insert comprises plastic.

20. A plug-in oil diffuser device, comprising:
   a) a housing;
   b) a plug extending from the housing and configured to be plugged into a wall electrical outlet;
   c) a face of the housing facing outwardly opposite the plug, the face being vertically oriented;
   d) an aperture in the face of the housing;
   e) a heat plate disposed in the housing and electrically coupled to the plug, the heat plate spanning the aperture in the housing and the aperture exposing the heat plate, the heat plate configured to receive an absorbent pad with oil therein, the heat plate being vertically oriented;
   f) the heat plate abutting an interior of the face around a perimeter of the aperture;
   g) a seal disposed between the heat plate and the face configured to resist oil seepage from the pad into the housing;
   h) a chamfer in the face at the perimeter of the aperture configured to assist insertion and remove of the pad;
   i) a projection extending from the housing opposite the plug, and surrounding the heat plate, and having an exterior;
   j) a non-plastic faceplate removably coupled to the projection of the housing and covering the face and the heat plate;
   k) the non-plastic faceplate having cavity therein with an opening to receive the projection of the housing;
   l) an annular insert carried by the non-plastic faceplate in the opening of the non-plastic faceplate, the annular insert securing the non-plastic faceplate to the housing, and the annular insert having an exterior secured to the non-plastic faceplate and an interior removably secured to the exterior of the projection of the housing;
   m) a notch and a tab between the exterior of the annular insert and the opening of the non-plastic faceplate with the tab extending from one of the annular insert or the non-plastic faceplate into the notch in the other of the non-plastic faceplate or the annular insert;
   n) a releasable fastener formed between the interior of the annular insert and the exterior of the projection of the housing;
   o) holes in the non-plastic faceplate opposite the opening configured to allow release of fragrance from the pad;
   p) a light source disposed in the housing and electrically coupled to the plug; and
   q) at least a portion of the housing, including a portion of the face or the projection disposed inside the non-plastic faceplate, is at least translucent configured to pass light from the light source therethrough.

* * * * *